United States Patent [19]

Rowles et al.

[11] Patent Number: 4,732,598
[45] Date of Patent: Mar. 22, 1988

[54] DEPHLEGMATOR PROCESS FOR NITROGEN REJECTION FROM NATURAL GAS

[75] Inventors: Howard C. Rowles, Center Valley; Ruth A. Davis, Allentown, both of Pa.

[73] Assignee: Air Products and Chemicals, Inc., Allentown, Pa.

[21] Appl. No.: 929,045

[22] Filed: Nov. 10, 1986

[51] Int. Cl.$^4$ .................................................. F25J 3/04
[52] U.S. Cl. ........................................... 62/28; 62/29; 62/39; 62/41; 62/44
[58] Field of Search ............... 62/9, 11, 23, 24, 27–29, 62/31, 32, 36, 38, 39, 41, 42, 44

[56] References Cited

U.S. PATENT DOCUMENTS

| | | | |
|---|---|---|---|
| 3,392,536 | 7/1968 | Smith | 62/29 X |
| 3,516,262 | 7/1970 | Bernstein | 62/28 |
| 3,520,143 | 7/1970 | Becker | 62/28 |
| 3,568,458 | 3/1971 | Hoffman et al. | 62/31 |
| 3,568,459 | 3/1971 | Hoffman et al. | 62/34 |
| 3,683,634 | 8/1972 | Streich | 62/29 |
| 3,797,261 | 3/1974 | Juncker et al. | 62/40 |
| 4,002,042 | 1/1977 | Pryor et al. | 62/28 |
| 4,158,556 | 6/1979 | Yearout | 62/28 |
| 4,270,939 | 6/1981 | Rowles et al. | 62/39 X |
| 4,270,940 | 6/1981 | Rowles et al. | 62/28 |
| 4,411,677 | 10/1983 | Pervier et al. | 62/25 |
| 4,415,345 | 11/1983 | Swallow | 62/28 |
| 4,455,158 | 6/1984 | Vines et al. | 62/28 |
| 4,504,295 | 3/1985 | Davis et al. | 62/30 |
| 4,519,825 | 5/1985 | Bernhard et al. | 62/28 |
| 4,525,187 | 6/1985 | Woodward et al. | 62/31 |

Primary Examiner—Steven E. Warner
Attorney, Agent, or Firm—Willard Jones, II; James C. Simmons; William F. Marsh

[57] ABSTRACT

A process is disclosed for the rejection of nitrogen from natural gas with the optional recovery of natural gas liquids. The process of the present invention employs a dephlegmator which provides a high purity nitrogen reflux for a low pressure distillation column and provides subcooling of the feed and reflux to the low pressure column and reboiling of the low pressure column. The dephlegmator of the present invention combines the high pressure column and three heat exchangers of a conventional double column process into a single, compact unit, with corresponding reductions in interconnecting piping and capital investment.

17 Claims, 2 Drawing Figures

DEPHLEGMATOR PROCESS FOR NITROGEN REJECTION FROM NATURAL GAS

TECHNICAL FIELD

The present invention relates to a process for the rejection of nitrogen from fixed or variable nitrogen content natural gas streams with high recovery of methane.

BACKGROUND OF THE INVENTION

Petroleum production methods currently are utilizing high pressure nitrogen injection to maintain well head pressure for enhanced oil and gas recovery. As nitrogen is injected, the natural gas from the well containing methane and associated hydrocarbon liquids also contains nitrogen which increases in amount over the life of the nitrogen injection project. There are also gas fields which naturally contain high levels of nitrogen at an essentially constant or fixed composition. For this reason, natural gas containing nitrogen must be separated to reject the nitrogen and form purified natural gas feedstocks suitable for utilization as fuel or chemical feedstocks.

Several processes have either been proposed or commercially utilized to reject nitrogen from natural gas streams containing fixed or variable nitrogen contents.

U.S. Pat. No. 3,516,262 discloses a process, for separating methane from mixtures of methane and nitrogen. In the process, a mixture of methane and nitrogen is separated in an initial separation stage to produce a cold nitrogen vapor and a methane-rich liquid. The methane-rich liquid is fed to a fractionating column in heat exchange relation with the initial separation stage. The cold nitrogen from the initial separation stage is recycled at a reduced temperature in heat exchange relationship along the upper portion of the fractionating column and the inital separation zone. The liquid-vapor mixture in the lower section of the initial separation zone provides heat and reboiler duty to the lower portion of the fractionating column. The initial separation zone and fractionating column are operated under conditions to effect a "differential" distillation in the column.

U.S. Pat. No. 3,683,634 discloses a process which especially suitable for natural gas containing a low concentration, i.e. 1 mole percent or less, of carbon dioxide from which the nitrogen and part of the methane are to be recovered in substantially pure form by separation in a two-stage rectification zone. In accordance with the process, a portion of a pressurized gas mixture which contains one or more components that are precipitated in solid form during cool-down, is separated in a prefractionation zone into a fraction essentially free of such components and a fraction containing a higher concentration of such components.

U.S. Pat. No. 3,797,261 discloses the separation of natural gas containing nitrogen into a low-nitrogen fraction and a high nitrogen fraction by distillation in a single distillation column by expanding the high-nitrogen fraction with the performance of work and using the resulting refrigeration to condense vapor in the upper section of the column while additional reflux is provided by vaporizing a recycle medium in heat exchange relation with vapor in the column. The high-nitrogen mixture, having been expanded, is exhausted at atmospheric pressure.

U.S. Pat. No. 4,158,556 discloses a process for separating nitrogen from natural gas hydrocarbons by using a column with a single fractionation zone operating at feed pressure, work expanding the overhead nitrogen to produce a cold nitrogen stream, utilizing the resultant cold nitrogen stream in continuous indirect heat exchange with column vapors to provide reflux, and generating additional reflux by boiling liquid bottoms in continuous indirect heat exchange with the lower section of the column.

U.S. Pat. No. 4,411,677 discloses a process for rejecting nitrogen from a natural gas feed containing nitrogen over a broad range of compositions, under elevated pressure using a single distillation column, and a closed loop methane heat pump which reboils and refluxes the column. An intermediate reflux condenser is cooled by both the heat pump and overhead nitrogen stream of the column. A mixed cryogenic refrigerant can be used in the heat pump as an alternative to the methane heat pump medium. The process provides a high methane recovery over the entire feed range, and provides a pressurized nitrogen product stream that can be used for recycling and reinjection to an oil or gas well to improve well head pressure.

U.S. Pat. No. 4,415,345 discloses a process for separating by rectification, low concentration nitrogen from natural gases having a gradually increasing nitrogen concentration which employs a nitrogen heat pump cycle to generate the necessary liquid reflux for a fractionation column. The process disclosed in the patent is compatible for use with both single column and double column process arrangements.

U.S. Pat. No. 4,455,158 discloses a process for cooling a multicomponent gas stream containing variable amounts of the components by passing the gas stream through a heat exchange relationship with a fluid coolant stream so that carry-up of the condensed phase is maintained without the condensed phase backmixing over the compositional range of the multicomponent gas stream. The gas stream is cooled by passing it through a cold-end up heat exchanger having a serpentine pathway for the multicomponent gas stream comprising a series of horizontal passes separated by horizontal dividers and alternatingly connected by turnaround passes at each end, the cross-sectional area of at least one horizontal pass nearer the cold end being less than the cross-sectional area of a horizontal pass nearer the warm-end. The process is especially applicable to cooling a natural gas stream having a variable nitrogen content in a nitrogen rejection process.

U.S. Pat. No. 4,504,295 discloses a process for the recovery of methane, nitrogen and natural gas liquids from a natural gas feed stream wherein the recovery can be made by the integration of a nitrogen rejection stage including a heat pump driven distillation column and a natural gas liquids recovery stage. Nitrogen can be rejected over a wide range of nitrogen concentrations in the feed stream.

SUMMARY OF THE INVENTION

The present invention relates to a process for the rejection of nitrogen from a pressurized natural gas feed stream containing nitrogen by cryogenic distillation in which the feed stream is cooled and optionally expanded in order to partially condense the feed stream. This partially condensed feed stream is then fed to a separator wherein it is separated into a liquid phase and a gaseous phase. The gaseous phase from the separator is further cooled in a dephlegmator wherein the gaseous phase is partially condensed and rectified to provide a non-condensed portion enriched in nitrogen and condensed liquids enriched in methane; gravity separates the partially condensed gaseous phase into the condensed and non-condensed portions. The methane enriched condensed portion is returned to the separator wherein it becomes part of the liquid phase. The nitrogen enriched non-condensed portion of the gaseous phase is then further cooled, condensed, optionally subcooled, expanded and fed to a low pressure distillation column as reflux.

The liquid phase from the separator, which includes the methane enriched condensed portion of the gaseous phase from the dephlegmator, is subcooled in the dephlegmator, expanded, and fed to an intermediate location of the low pressure distillation column.

A first portion of a methane rich bottoms liquid is removed from the bottom of the low pressure distillation column, at least partially vaporized in the dephlegmator thereby providing refrigeration duty to the dephlegmator, and returned to the bottom of the low pressure distillation column thereby providing reboiler duty to the low pressure distillation column. A second portion of the methane rich bottoms liquid is removed from the bottom of the low pressure distillation column, pumped to an elevated pressure, warmed in order to recover refrigeration value from the second portion and then removed from the process as a methane product.

The nitrogen rich overhead vapor is removed from the top of the low pressure distillation column, warmed in order to recover refrigeration value from the overhead vapor, and removed from the process as a nitrogen product.

Optionally, in some circumstances, a portion of the nitrogen enriched non-condensed stream may be split off and expanded to provide additional refrigeration to the process. This expanded enriched nitrogen stream can be returned to the process by combining the expanded enriched nitrogen with the overhead vapor from the low pressure distillation.

Optionally, natural gas liquids can be removed from the feed stream prior to the nitrogen rejection portion of the process.

DETAILED DESCRIPTION OF THE PRESENT INVENTION

The present invention is a low capital cost, energy efficient process for the rejection of nitrogen from natural gas, particularly if a relatively small plant size is required and where high pressure nitrogen product is not required and the rejected nitrogen can be vented to the atmosphere. Basically, the present invention is a nitrogen rejection process of the type wherein a double distillation column would be utilized; the present invention being the replacement of the high pressure column and the reboiler and condenser for the double column with a single dephlegmator.

Figure 1:
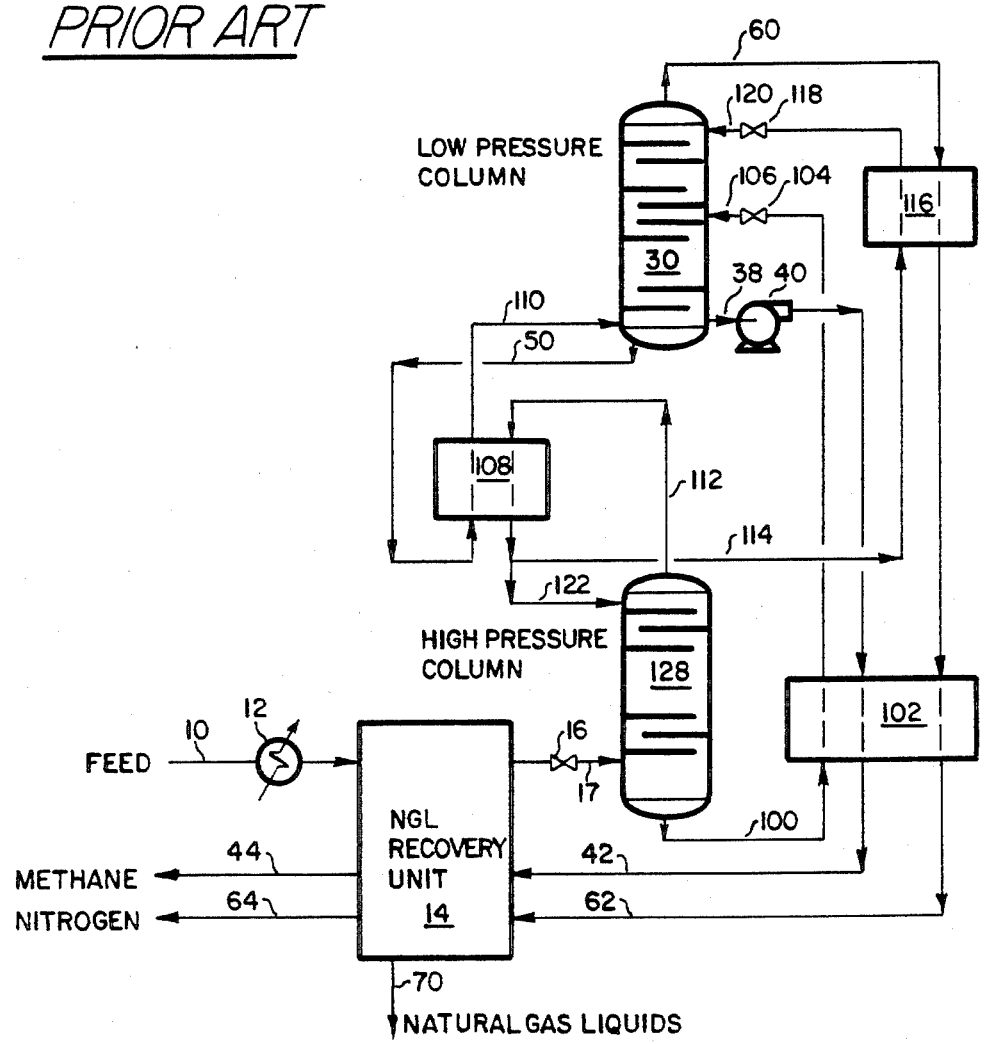
FIG. 1 is a schematic drawing of a double distillation column process for the rejection of nitrogen from a natural gas stream utilizing a prior art process.

With reference to FIG. 1, a nitrogen rejection process is shown which utilizes a double column distillation process and incorporates a natural gas liquids recovery unit upstream of the nitrogen rejection process. In this prior art process, a pressurized natural gas - nitrogen feed stream, in line 10 is fed to refrigerant heat exchanger 12 and natural gas liquids (NGL) recovery unit 14, and reduced in pressure in J-T valve 16, if necessary. The NGL recovery unit, which is typically a combination of heat exchangers, separators and a fractionation column, can be any of such type which serves the purpose of recovering natural gas liquids. One such unit is described in U.S. Pat. No. 4,504,295, the specification of which is incorporated by reference. The cooled, natural gas liquids are recovered via line 70. Expanded feed stream in line 17 is fed to the bottom of high pressure distillation column 128.

The methane enriched bottoms liquid of high pressure column 128 in line 100 is subcooled in heat exchanger 102, reduced in pressure in J-T valve 104 and fed to an intermediate location of low pressure distillation column 30, via line 106. The nitrogen enriched overhead vapor of high pressure column 128 is removed in line 112, cooled and condensed in heat exchanger 108 and split into two substreams. The first substream in line 114 is subcooled in heat exchanger 116, reduced in pressure in J-T valve 118 and fed to an upper location of low pressure distillation column 30 as reflux, via line 120. The second substream is fed to an upper location of high pressure distillation column 128 as reflux, via line 122.

A portion of the methane rich bottoms liquid of low pressure distillation column 30 is removed in line 50, at least partially vaporized in heat exchanger 108 and reintroduced into a lower location of low pressure distillation column 30, via line 110. The remaining portion of the bottoms liquid of low pressure distillation column 30, i.e. a high methane content product stream, is removed in line 38, pumped to a suitable pressure in pump 40, warmed in heat exchanger 102 and fed to NGL recovery unit 14, via line 42. The overhead vapor of low pressure distillation column 30, i.e. a nitrogen product stream, is removed in line 60, warmed in heat exchangers 116 and 102, and fed to NGL recovery unit 14, via line 62. These streams in lines 42 and 62 provide refrigeration duty to NGL recovery unit 14.

The high methane content product stream in line 42 may be combined with any methane product from NGL recovery unit 14 to produce a methane product stream which is removed from NGL recovery unit 14 in line 44. The nitrogen product stream is removed from NGL recovery unit 14 via line 64. The natural gas liquids are removed from NGL recovery unit 14 via line 70.

Figure 2:
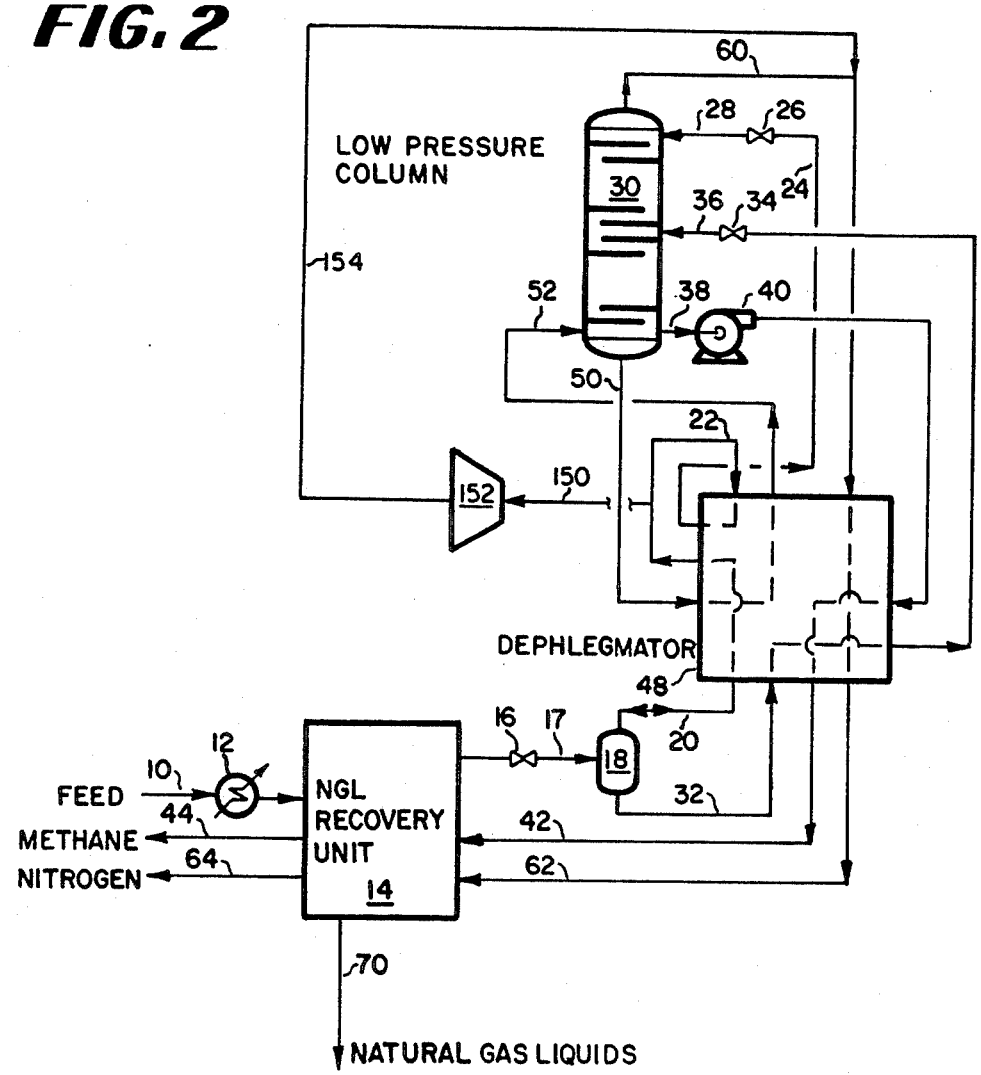
FIG. 2 is a schematic drawing of the process of the present invention.

The present invention, which incorporates heat exchangers 102, 108 and 116 and high pressure distillation column 128 into single dephlegmator unit 48, is shown in FIG. 2 where items common to FIG. 1 are numbered the same. With reference to FIG. 2, a pressurized natural gas-nitrogen feed stream, in line 10 is fed to refrigerant heat exchanger 12 and natural gas liquids (NGL) recovery unit 14, and reduced in pressure in J-T valve 16, if necessary. As stated before, the NGL recovery unit can be any of such type which serves the purpose of recovering natural gas liquids. The recovery of natural gas liquids is an optional step in the present invention. The cooled, natural gas liquids are recovered via line 70 while the expanded feed stream in line 17 is fed to separator 18.

The overhead vapor of separator 18 in line 20 is fed to dephlegmator 48 wherein it is cooled, partially condensed and rectified to provide a non-condensed nitrogen enriched portion and a condensed methane enriched portion. The methane enriched condensed portion of the overhead of separator 18 returns to separator 18 via line 20. It is important to note that line 20 has two way flow, an upward flow of vapor from separator 18 and a downward flow of liquid condensed in dephlegmator 48 returning to separator 18. The nitrogen enriched non-condensed portion of the overhead from separator 18 is removed from dephlegmator 48, reintroduced at another location in dephlegmator 48 via line 22 where it is further cooled, condensed and subcooled, if desirable. The condensed nitrogen stream removed from dephlegmator 48 via line 24 is reduced in pressure in J-T valve 26 and introduced as reflux to low pressure distillation column 30 via line 28. As shown by dotted lines in FIG. 2, in some circumstances, a portion of the nitrogen enriched non-condensed stream in line 22 may be sent, via line 150, to expander 152 to provide additional refrigeration to the process. This expanded enriched nitrogen stream can be returned, via line 154, to the process by combining the expanded enriched nitrogen with the overhead from low pressure distillation column 30 in line 60.

The bottoms liquid of separator 18 in line 32 is fed to dephlegmator 48, wherein it is cooled, reduced in pressure in J-T valve 34 and introduced to an intermediate location of low pressure distillation column 30.

A portion of the methane rich bottoms liquid of low pressure distillation column 30 is removed in line 50, at least partially vaporized in dephlegmator 48 and reintroduced into a lower location of low pressure distillation column 30, via line 52. The remaining portion of the bottoms liquid of low pressure distillation column 30, i.e. a high methane content product stream, is removed in line 38, pumped to an elevated pressure in pump 40, warmed in dephlegmator 48 and fed to NGL recovery unit 14, via line 42. The overhead vapor of low pressure distillation column 30, i.e. a nitrogen product stream, is removed in line 60, warmed in dephlegmator 48, and fed to NGL recovery unit 14, via line 62. These streams in lines 42 and 62 provide refrigeration duty to NGL recovery unit 14.

The high methane content product stream in line 42 may be combined with any methane product from NGL recovery unit 14 to produce a methane product stream which is removed from NGL recovery unit 14 in line 44. The nitrogen product stream is removed from NGL recovery unit 14 via line 64. The natural gas liquids are removed from NGL recovery unit 14 via line 70.

As can be seen from a comparison of the prior art process as depicted in FIG. 1 and the present invention as depicted in FIG. 2, the present invention results in a significant reduction in piping and equipment. This reduction is achieved by combining high pressure column 128, heat exchanger (reboiler-condenser) 108, heat exchanger (low pressure column feed subcooler) 102 and heat exchanger (low pressure column reflux subcooler) 116 into dephlegmator 48. Dephlegmator 48 is considerable shorter than high pressure column 128, resulting in a smaller cold box height and smaller capital costs. The present invention requires the same or lower energy input as the prior art double column process, which is know to be highly energy efficient for this type of application.

EXAMPLE

In order to demonstrate the efficacy of the present invention, a heat and material balance was computer simulated. The following example is a summation of the computer simulation.

A material balance was generated for the process of the present invention for a nitrogen-natural gas feed stream having a composition of approximately 46% nitrogen, 48.2% methane and 5.8% natural gas liquids and a pressure of 1300 psig. The material balance, which is listed in Table I, details stream conditions, i.e. pressure, temperature and flow rate, along with stream compositions for selected streams throughout the process.

TABLE I

| Stream Number | Phase** | Temperature °F. | Pressure psia | Total Flow Rate #mol/hr | $N_2$ Flow Rate #mol/hr | $C_1$ Flow Rate #mol/hr | $C_2$ Flow Rate #mol/hr | $C_3$ Flow Rate #mol/hr | $C_4$ Flow Rate #mol/hr | $C_5$ Flow Rate #mol/hr | $C_6$ Flow Rate #mol/hr |
|---|---|---|---|---|---|---|---|---|---|---|---|
| 10 | V | 100 | 1,315 | 819.3 | 377.2 | 394.7 | 17.5 | 10.0 | 9.2 | 4.9 | 5.8 |
| 17 | V & L | −226 | 240 | 478.2 | 231.2 | 235.5 | 8.4 | 2.6 | 0.5 | NIL | NIL |
| 20 UP* | V | −226 | 240 | 162.6 | 129.4 | 33.2 | NIL | NIL | NIL | NIL | NIL |
| 20 DN* | L | −235 | 240 | 95.2 | 62.3 | 32.9 | NIL | NIL | NIL | NIL | NIL |
| 22 | V | −257 | 240 | 67.4 | 67.1 | 0.3 | NIL | NIL | NIL | NIL | NIL |
| 28 | V & L | −305 | 36 | 67.4 | 67.1 | 0.3 | NIL | NIL | NIL | NIL | NIL |
| 32 | L | −233 | 240 | 410.8 | 164.1 | 235.2 | 8.4 | 2.6 | 0.5 | NIL | NIL |
| 36 | V & L | −289 | 36.3 | 410.8 | 164.1 | 235.2 | 8.4 | 2.6 | 0.5 | NIL | NIL |
| 38 | L | −265 | 37 | 270.3 | 23.5 | 235.3 | 8.4 | 2.6 | 0.5 | NIL | NIL |
| 42 | L | −233 | 396 | 270.3 | 23.5 | 235.3 | 8.4 | 2.6 | 0.5 | NIL | NIL |
| 44 | V | 100 | 915 | 587.5 | 169.5 | 394.5 | 16.3 | 5.3 | 1.7 | 0.2 | NIL |
| 50 | L | −288 | 36.5 | 378.3 | 102.4 | 264.4 | 8.4 | 2.6 | 0.5 | NIL | NIL |
| 52 | V & L | −265 | 36.5 | 378.3 | 102.4 | 264.4 | 8.4 | 2.6 | 0.5 | NIL | NIL |
| 60 | V | −305 | 36 | 207.8 | 207.6 | 0.2 | NIL | NIL | NIL | NIL | NIL |
| 62 | V | −233 | 33 | 207.8 | 207.6 | 0.2 | NIL | NIL | NIL | NIL | NIL |
| 64 | V | 29 | 20 | 207.8 | 207.6 | 0.2 | NIL | NIL | NIL | NIL | NIL |
| 70 | L | 287 | 450 | 24.0 | NIL | NIL | 1.2 | 4.7 | 7.6 | 4.7 | 5.8 |

*Stream 20 has two way flow: vapor-up, liquid down
**V = Vapor
L = Liquid
V & L = Vapor & Liquid The present invention has been described with reference to a preferred embodiment thereof. However, this embodiment should not be considered a limitation on the scope of the invention, which scope should be ascertained by the following claims.

We claim:

1. A process for the rejection of nitrogen from a pressurized natural gas feed stream containing nitrogen by cryogenic distillation comprising the steps of:
   (a) cooling the pressurized natural gas feed stream containing nitrogen whereby said stream partially condenses;

(b) separating said feed stream into a liquid phase and a gaseous phase in a separator;

(c) cooling said gaseous phase in a dephlegmator whereby said gaseous phase is partially condensed and rectified and whereby gravity separates said partially condensed gaseous phase into a methane enriched condensed portion and a nitrogen enriched non-condensed portion;

(d) returning said methane enriched condensed portion to said separator in step (b) whereby said methane enriched condensed portion becomes part of said liquid phase;

(e) cooling, condensing and expanding said nitrogen enriched non-condensed portion and feeding said cooled, condensed, expanded, nitrogen enriched portion to a low pressure distillation column as reflux;

(f) subcooling the liquid phase of step (d) in said dephlegmator, expanding said subcooled liquid phase, and feeding said expanded subcooled liquid phase to an intermediate location of said low pressure distillation column;

(g) removing a first portion of a bottoms liquid from the bottom of said low pressure distillation column, at least partially vaporizing said first portion in said dephlegmator thereby providing refrigeration duty to said dephlegmator, and returning said partially vaporized first portion to the bottom of the low pressure distillation column thereby providing reboiler duty to said low pressure distillation column;

(h) removing a second portion of the bottoms liquid from the bottom of said low pressure distillation column, pumping said second portion to an elevated pressure, warming said second portion thereby recovering refrigeration value from said second portion, and removing said pumped, warmed, second portion from the process as a methane product; and (i) removing an overhead vapor from the top of said low pressure distillation column, warming said overhead vapor thereby recovering refrigeration value from said overhead, and removing said warmed overhead vapor from the process as a nitrogen product.

2. The process according to claim 1 which further comprises the step of recovering natural gas liquids from said pressurized natural gas feed stream prior to cooling said feed in step (a).

3. The process according to claim 1 which further comprises subcooling said cooled, condensed nitrogen enriched portion of step (e) prior to expanding.

4. The process according to claim 1 which further comprises expanding said cooled pressurized natural gas feed stream of step (a).

5. The process according to claim 4 which further comprises the step of recovering natural gas liquids from said pressurized natural gas feed stream prior to cooling and expanding said feed in step (a).

6. The process according to claim 5 which further comprises subcooling said cooled, condensed nitrogen enriched portion of step (e) prior to expanding.

7. A process for the rejection of nitrogen from a pressurized natural gas feed stream containing nitrogen by cryogenic distillation comprising the steps of:

(a) cooling the pressurized natural gas feed stream containing nitrogen whereby said stream partially condenses;

(b) separating said feed stream into a liquid phase and a gaseous phase in a separator;

(c) cooling said gaseous phase in a dephlegmator whereby said gaseous phase is partially condensed and rectified and whereby gravity separates said partially condensed gaseous phase into a methane enriched condensed portion and a nitrogen enriched non-condensed portion;

(d) returning said methane enriched condensed portion to said separator in step (b) whereby said methane enriched condensed portion becomes part of said liquid phase;

(e) separating said nitrogen enriched non-condensed portion of step (c) into a first substream and a second substream;

(f) cooling, condensing and expanding said first substream and feeding said cooled, condensed, expanded, first substream to a low pressure distillation column as reflux;

(g) expanding said second substream to provide refrigeration;

(h) subcooling the liquid phase of step (d) in said dephlegmator, expanding said subcooled liquid phase, and feeding said expanded subcooled liquid phase to an intermediate location of said low pressure distillation column;

(i) removing a first portion of a bottoms liquid from the bottom of said low pressure distillation column, at least partially vaporizing said first portion in said dephlegmator thereby providing refrigeration duty to said dephlegmator, and returning said partially vaporized first portion to the bottom of the low pressure distillation column thereby providing reboiler duty to said low pressure distillation column;

(j) removing a second portion of the bottoms liquid from the bottom of said low pressure distillation column, pumping said second portion to an elevated pressure, warming said second portion thereby recovering refrigeration value from said second portion, and removing said pumped, warmed, second portion from the process as a methane product; and (k) removing an overhead vapor from the top of said low pressure distillation column, warming said overhead vapor thereby recovering refrigeration value from said overhead, and removing said warmed overhaad vapor from the process as a nitrogen product.

8. The process according to claim 7 which further comprises expanding said cooled pressurized natural gas feed stream of step (a).

9. The process according to claim 7 which further comprises combining said second substream from step (g) with said overhead vapor of step (k) prior to warming said overhead vapor to recover refrigeration.

10. The process according to claim 7 which further comprises subcooling said cooled, condensed first substream of step (f) prior to expanding.

11. The process according to claim 7 which further comprises the step of recovering natural gas liquids from said pressurized natural gas feed stream prior to cooling said feed in step (a).

12. The process according to claim 11 which further comprises combining said second substream from step (g) with said overhead vapor of step (k) prior to warming said overhead vapor to recover refrigeration.

13. The process according to claim 11 which further comprises subcooling said cooled, condensed first substream of step (f) prior to expanding.

14. The process according to claim 11 which further comprises expanding said cooled pressurized natural gas feed stream of step (a).

15. The process according to claim 14 which further comprises subcooling said cooled, condensed first substream of step (f) prior to expanding.

16. The process according to claim 14 which further comprises combining said second substream from step (g) with said overhead vapor of step (k) prior to warming said overhead vapor to recover refrigeration.

17. The process according to claim 16 which further comprises subcooling said cooled, condensed first substream of step (f) prior to expanding.

* * * * *